(12) United States Patent
Beira

(10) Patent No.: US 10,864,049 B2
(45) Date of Patent: Dec. 15, 2020

(54) DOCKING SYSTEM FOR MECHANICAL TELEMANIPULATOR

(71) Applicant: DistalMotion SA, Lausanne (CH)

(72) Inventor: Ricardo Daniel Rita Beira, Lausanne (CH)

(73) Assignee: Distalmotion SA, Epalinges (CH)

( * ) Notice: Subject to any disclaimer, the term of this patent is extended or adjusted under 35 U.S.C. 154(b) by 630 days.

(21) Appl. No.: 15/536,539

(22) PCT Filed: Dec. 18, 2015

(86) PCT No.: PCT/IB2015/002524
§ 371 (c)(1),
(2) Date: Jun. 15, 2017

(87) PCT Pub. No.: WO2016/097871
PCT Pub. Date: Jun. 23, 2016

(65) Prior Publication Data
US 2018/0000544 A1 Jan. 4, 2018

Related U.S. Application Data

(60) Provisional application No. 62/094,075, filed on Dec. 19, 2014.

(51) Int. Cl.
*A61B 34/00* (2016.01)
*A61B 17/00* (2006.01)
(Continued)

(52) U.S. Cl.
CPC .............. *A61B 34/30* (2016.02); *A61B 34/70* (2016.02); *A61B 17/00234* (2013.01); *B25J 3/00* (2013.01)

(58) Field of Classification Search
CPC ......... A61B 34/30; A61B 34/70; A61B 34/71; A61B 34/37; A61B 34/74; B25J 3/00; B25J 3/02; B25J 3/04
See application file for complete search history.

(56) References Cited

U.S. PATENT DOCUMENTS 2,764,301 A  9/1956 Goertz et al.
2,771,199 A  11/1956 Jelatis
(Continued)

FOREIGN PATENT DOCUMENTS

CN  101584594 A  11/2009
CN  101637402 A  2/2010
(Continued)

OTHER PUBLICATIONS

US 9,232,978 B2, 01/2016, Shellenberger et al. (withdrawn)
(Continued)

*Primary Examiner* — Majid Jamialahmadi
(74) *Attorney, Agent, or Firm* — Eversheds Sutherland (US) LLP; Christopher C. Bolten; Albert K. Heng

(57) ABSTRACT

A docking system for a mechanical telemanipulator is provided, optionally to be used with a mechanical telemanipulator with a master-slave configuration. The docking system is configured to allow for safe and secure immobilization of a handle or master manipulator of a mechanical telemanipulator with a master-slave configuration so as to prevent movement of a slave manipulator or instrument. While the docking element can be deployed on any mechanical telemanipulator, it can advantageously be used on a surgical platform comprising a mechanical telemanipulator with a master-slave configuration. In this context, the docking system can be used to secure the handle portion or master manipulator of the surgical platform to safely prevent undesirable movement of a slave manipulator or surgical instrument.

11 Claims, 10 Drawing Sheets

(51) Int. Cl.
   *B25J 3/00* (2006.01)
   *A61B 34/30* (2016.01)

(56) References Cited

U.S. PATENT DOCUMENTS

| | | |
|---|---|---|
| 2,774,488 A | 12/1956 | Goertz |
| 2,846,084 A | 8/1958 | Goertz et al. |
| 3,095,096 A | 6/1963 | Chesley |
| 3,212,651 A | 10/1965 | Specht et al. |
| 3,065,863 A | 11/1965 | Saunders, Jr. |
| 3,261,480 A | 7/1966 | Haaker et al. |
| 3,297,172 A | 1/1967 | Haaker et al. |
| 3,391,801 A | 7/1968 | Haaker |
| 3,425,569 A | 2/1969 | Haaker et al. |
| 4,221,516 A | 9/1980 | Haaker et al. |
| 4,756,655 A | 7/1988 | Jameson |
| 5,147,357 A | 9/1992 | Rose et al. |
| 5,176,352 A | 1/1993 | Braun |
| 5,207,114 A | 5/1993 | Salisbury et al. |
| 5,209,747 A | 5/1993 | Knoepfler |
| 5,304,203 A | 4/1994 | El-Mallawany et al. |
| 5,308,358 A | 5/1994 | Bond et al. |
| 5,330,502 A | 7/1994 | Hassler et al. |
| 5,368,606 A | 11/1994 | Marlow et al. |
| 5,383,888 A | 1/1995 | Zvenyatsky et al. |
| 5,484,435 A | 1/1996 | Fleenor et al. |
| 5,599,151 A | 2/1997 | Daum et al. |
| 5,603,723 A | 2/1997 | Aranyi et al. |
| 5,631,973 A | 5/1997 | Green |
| 5,649,955 A | 7/1997 | Hashimoto et al. |
| 5,649,956 A | 7/1997 | Jensen et al. |
| 5,710,870 A | 1/1998 | Ohm et al. |
| 5,716,352 A | 2/1998 | Viola et al. |
| 5,735,874 A | 4/1998 | Measamer et al. |
| 5,784,542 A | 7/1998 | Ohm et al. |
| 5,792,045 A | 8/1998 | Adair |
| 5,797,900 A | 8/1998 | Madhani et al. |
| 5,810,716 A | 9/1998 | Mukherjee et al. |
| 5,810,805 A | 9/1998 | Sutcu et al. |
| 5,828,813 A | 10/1998 | Ohm |
| 5,908,436 A | 6/1999 | Cuschieri et al. |
| 5,931,832 A | 8/1999 | Jensen |
| 5,951,587 A | 9/1999 | Qureshi et al. |
| 5,976,122 A | 11/1999 | Madhani et al. |
| 6,026,701 A | 2/2000 | Reboulet |
| 6,063,095 A | 5/2000 | Wang et al. |
| 6,132,368 A | 10/2000 | Cooper |
| 6,197,017 B1 | 3/2001 | Brock et al. |
| 6,206,903 B1 | 3/2001 | Ramans |
| 6,233,504 B1 | 5/2001 | Das et al. |
| 6,281,651 B1 | 8/2001 | Haanpaa et al. |
| 6,312,435 B1 | 11/2001 | Wallace et al. |
| 6,331,181 B1 | 12/2001 | Tierney et al. |
| 6,358,249 B1 | 3/2002 | Chen et al. |
| 6,361,534 B1 | 3/2002 | Chen et al. |
| 6,364,879 B1 | 4/2002 | Chen et al. |
| 6,371,952 B1 | 4/2002 | Madhani et al. |
| 6,394,998 B1 | 5/2002 | Wallace et al. |
| 6,435,794 B1 | 8/2002 | Springer |
| 6,459,926 B1 | 10/2002 | Nowlin et al. |
| 6,491,701 B2 | 12/2002 | Tierney et al. |
| 6,554,844 B2 | 4/2003 | Lee et al. |
| 6,587,750 B2 | 7/2003 | Gerbi et al. |
| 6,594,552 B1 | 7/2003 | Nowlin et al. |
| 6,671,581 B2 | 12/2003 | Niemeyer et al. |
| 6,699,177 B1 | 3/2004 | Wang et al. |
| 6,786,896 B1 | 9/2004 | Madhani et al. |
| 6,788,999 B2 | 9/2004 | Green |
| 6,840,938 B1 | 1/2005 | Morley et al. |
| 6,850,817 B1 | 2/2005 | Green |
| 6,852,107 B2 | 2/2005 | Wang et al. |
| 6,879,880 B2 | 4/2005 | Nowlin et al. |
| 6,902,560 B1 | 6/2005 | Morley et al. |
| 6,913,613 B2 | 7/2005 | Schwarz et al. |
| 6,951,535 B2 | 10/2005 | Ghodoussi et al. |
| 6,991,627 B2 | 1/2006 | Madhani et al. |
| 6,994,708 B2 | 2/2006 | Manzo |
| 7,048,745 B2 | 5/2006 | Tierney et al. |
| 7,083,571 B2 | 8/2006 | Wang et al. |
| 7,090,637 B2 | 8/2006 | Danitz et al. |
| 7,101,363 B2 | 9/2006 | Nishizawa et al. |
| 7,204,836 B2 | 4/2007 | Wagner et al. |
| 7,232,440 B2 | 6/2007 | Dumbauld et al. |
| 7,241,289 B2 | 7/2007 | Braun |
| 7,306,597 B2 | 12/2007 | Manzo |
| 7,316,681 B2 | 1/2008 | Madhani et al. |
| 7,338,513 B2 | 3/2008 | Lee et al. |
| 7,364,582 B2 | 4/2008 | Lee |
| 7,373,219 B2 | 5/2008 | Nowlin et al. |
| 7,398,707 B2 | 7/2008 | Morley et al. |
| 7,481,824 B2 | 1/2009 | Boudreaux et al. |
| 7,549,998 B2 | 6/2009 | Braun |
| 7,594,912 B2 | 9/2009 | Cooper et al. |
| 7,608,039 B1 | 10/2009 | Todd |
| 7,615,002 B2 | 11/2009 | Rothweiler et al. |
| 7,615,067 B2 | 11/2009 | Lee et al. |
| 7,674,255 B2 | 3/2010 | Braun |
| 7,699,855 B2 | 4/2010 | Anderson et al. |
| 7,756,036 B2 | 7/2010 | Druke et al. |
| 7,819,894 B2 | 10/2010 | Mitsuishi et al. |
| 7,824,401 B2 | 11/2010 | Manzo et al. |
| 7,828,798 B2 | 11/2010 | Buysse et al. |
| 7,833,156 B2 | 11/2010 | Williams et al. |
| 7,890,211 B2 | 2/2011 | Green |
| 7,914,521 B2 | 3/2011 | Wang et al. |
| 7,976,458 B2 | 7/2011 | Stefanchik et al. |
| 8,048,084 B2 | 11/2011 | Schneid |
| 8,105,320 B2 | 1/2012 | Manzo |
| 8,114,017 B2 | 2/2012 | Bacher |
| 8,137,263 B2 | 3/2012 | Marescaux et al. |
| 8,142,447 B2 | 3/2012 | Cooper et al. |
| 8,224,485 B2 | 7/2012 | Unsworth |
| 8,246,617 B2 | 8/2012 | Welt et al. |
| 8,267,958 B2 | 9/2012 | Braun |
| 8,287,469 B2 | 10/2012 | Stefanchik et al. |
| 8,292,889 B2 | 10/2012 | Cunningham et al. |
| 8,306,656 B1 | 11/2012 | Schaible et al. |
| 8,308,738 B2 | 11/2012 | Nobis et al. |
| 8,332,072 B1 | 12/2012 | Schaible et al. |
| 8,336,751 B2 | 12/2012 | Scirica |
| 8,347,754 B1 | 1/2013 | Veltri et al. |
| 8,353,898 B2 | 1/2013 | Lutze et al. |
| 8,357,161 B2 | 1/2013 | Mueller |
| 8,382,742 B2 | 2/2013 | Hermann et al. |
| 8,388,516 B2 | 3/2013 | Sholev |
| 8,403,832 B2 | 3/2013 | Cunningham et al. |
| 8,414,475 B2 | 4/2013 | Sholev |
| 8,418,904 B2 | 4/2013 | Wenchell et al. |
| 8,423,186 B2 | 4/2013 | Itkowitz et al. |
| 8,435,171 B2 | 5/2013 | Sholev |
| 8,496,152 B2 | 7/2013 | Viola |
| 8,518,024 B2 | 8/2013 | Williams et al. |
| 8,523,900 B2 | 9/2013 | Jinno et al. |
| 8,540,748 B2 | 9/2013 | Murphy et al. |
| 8,562,592 B2 | 10/2013 | Conlon et al. |
| 8,568,444 B2 | 10/2013 | Cunningham |
| 8,579,176 B2 | 11/2013 | Smith et al. |
| 8,591,397 B2 | 11/2013 | Berkelman et al. |
| 8,597,280 B2 | 12/2013 | Cooper et al. |
| 8,602,287 B2 | 12/2013 | Yates et al. |
| 8,603,077 B2 | 12/2013 | Cooper et al. |
| 8,616,431 B2 | 12/2013 | Timm et al. |
| 8,617,203 B2 | 12/2013 | Stefanchik et al. |
| 8,663,270 B2 | 3/2014 | Donnigan et al. |
| 8,668,689 B2 | 3/2014 | Dumbauld et al. |
| 8,668,702 B2 | 3/2014 | Awtar et al. |
| 8,690,755 B2 | 4/2014 | Sholev |
| 8,696,666 B2 | 4/2014 | Sanai et al. |
| 8,709,000 B2 | 4/2014 | Madhani et al. |
| 8,761,930 B2 | 6/2014 | Nixon |
| 8,768,509 B2 | 7/2014 | Unsworth |
| 8,792,688 B2 | 7/2014 | Unsworth |
| 8,801,752 B2 | 8/2014 | Fortier et al. |
| 8,816,628 B2 | 8/2014 | Nowlin et al. |

(56) References Cited

U.S. PATENT DOCUMENTS

| | | |
|---|---|---|
| 8,818,560 B2 | 8/2014 | Kishi |
| 8,821,480 B2 | 9/2014 | Burbank |
| 8,827,135 B2 | 9/2014 | Amid et al. |
| 8,828,046 B2 | 9/2014 | Stefanchik et al. |
| 8,845,517 B2 | 9/2014 | Russo |
| 8,845,622 B2 | 9/2014 | Paik et al. |
| 8,870,049 B2 | 10/2014 | Amid et al. |
| 8,870,867 B2 | 10/2014 | Walberg et al. |
| 8,887,979 B2 | 11/2014 | Mastri et al. |
| 8,894,674 B2 | 11/2014 | Balanev et al. |
| 8,919,348 B2 | 12/2014 | Williams et al. |
| 8,930,027 B2 | 1/2015 | Schaible et al. |
| 8,945,098 B2 | 2/2015 | Seibold et al. |
| 8,961,499 B2 | 2/2015 | Paik et al. |
| 8,961,514 B2 | 2/2015 | Garrison |
| 8,968,187 B2 | 3/2015 | Kleyman et al. |
| 8,989,844 B2 | 3/2015 | Cinquin et al. |
| 8,992,564 B2 | 3/2015 | Jaspers |
| 9,023,015 B2 | 5/2015 | Penna |
| 9,033,998 B1 | 5/2015 | Schaible et al. |
| 9,044,238 B2 | 6/2015 | Orszulak |
| 9,084,606 B2 | 7/2015 | Greep |
| 9,113,860 B2 | 8/2015 | Viola et al. |
| 9,113,861 B2 | 8/2015 | Martin et al. |
| 9,149,339 B2 | 10/2015 | Unsworth |
| 9,204,939 B2 | 12/2015 | Frimer et al. |
| 9,216,013 B2 | 12/2015 | Scirica et al. |
| 9,295,379 B2 | 3/2016 | Sholev |
| 9,307,894 B2 | 4/2016 | Von Grunberg et al. |
| 9,333,040 B2 | 5/2016 | Shellenberger et al. |
| 9,345,545 B2 | 5/2016 | Shellenberger et al. |
| 9,360,934 B2 | 6/2016 | Ruiz Morales et al. |
| 9,421,003 B2 | 8/2016 | Williams et al. |
| 9,474,580 B2 | 10/2016 | Hannaford et al. |
| 9,480,531 B2 | 11/2016 | Von Grunberg |
| 9,492,240 B2 | 11/2016 | Itkowitz et al. |
| 9,504,456 B2 | 11/2016 | Frimer et al. |
| 9,603,672 B2 | 3/2017 | Shellenberger et al. |
| 9,669,542 B2 | 6/2017 | Karguth et al. |
| 9,696,700 B2 | 7/2017 | Beira et al. |
| 9,757,204 B2 | 9/2017 | Frimer et al. |
| 9,757,206 B2 | 9/2017 | Frimer et al. |
| 9,763,741 B2 | 9/2017 | Alvarez et al. |
| 9,795,282 B2 | 10/2017 | Sholev et al. |
| 9,795,454 B2 | 10/2017 | Seeber et al. |
| 9,877,794 B2 | 1/2018 | Csiky |
| D816,243 S | 4/2018 | Barber |
| 9,937,013 B2 | 4/2018 | Frimer et al. |
| 9,943,372 B2 | 4/2018 | Sholev et al. |
| 10,028,792 B2 | 7/2018 | Frimer et al. |
| 10,039,609 B2 | 8/2018 | Frimer et al. |
| 10,052,157 B2 | 8/2018 | Frimer et al. |
| 10,064,691 B2 | 9/2018 | Frimer et al. |
| 10,071,488 B2 | 9/2018 | Robinson et al. |
| 10,092,164 B2 | 10/2018 | Sholev et al. |
| 10,092,359 B2 | 10/2018 | Beira et al. |
| 10,092,365 B2 | 10/2018 | Seeber |
| 10,136,956 B2 | 11/2018 | Seeber |
| 10,201,392 B2 | 2/2019 | Frimer et al. |
| 10,265,129 B2 | 4/2019 | Beira |
| 10,325,072 B2 | 6/2019 | Beira |
| 10,510,447 B2 | 12/2019 | Beira et al. |
| 10,548,680 B2 | 2/2020 | Beira |
| 10,568,709 B2 | 2/2020 | Beira |
| 10,646,294 B2 | 5/2020 | Beira |
| 2002/0040217 A1 | 4/2002 | Jinno |
| 2002/0049367 A1 | 4/2002 | Irion et al. |
| 2002/0072736 A1 | 6/2002 | Tierney et al. |
| 2002/0082612 A1 | 6/2002 | Moll |
| 2003/0013949 A1 | 1/2003 | Moll |
| 2003/0155747 A1 | 8/2003 | Bridges |
| 2003/0208186 A1 | 11/2003 | Moreyra |
| 2004/0049205 A1 | 3/2004 | Lee et al. |
| 2004/0236316 A1 | 11/2004 | Danitz et al. |
| 2004/0253079 A1 | 12/2004 | Sanchez |
| 2005/0096502 A1 | 5/2005 | Khalili |
| 2005/0204851 A1 | 9/2005 | Morley et al. |
| 2005/0240078 A1 | 10/2005 | Kwon et al. |
| 2006/0043698 A1 | 3/2006 | Bridges |
| 2006/0079884 A1 | 4/2006 | Manzo et al. |
| 2006/0178559 A1 | 8/2006 | Kumar et al. |
| 2006/0183975 A1 | 8/2006 | Saadat et al. |
| 2006/0219065 A1 | 10/2006 | Jinno et al. |
| 2006/0235436 A1 | 10/2006 | Anderson et al. |
| 2006/0253109 A1 | 11/2006 | Chu |
| 2007/0088340 A1 | 4/2007 | Brock et al. |
| 2007/0137371 A1 | 6/2007 | Devengenzo et al. |
| 2007/0156123 A1 | 7/2007 | Moll et al. |
| 2007/0208375 A1 | 9/2007 | Nishizawa et al. |
| 2007/0299387 A1 | 12/2007 | Williams et al. |
| 2008/0039255 A1 | 2/2008 | Jinno et al. |
| 2008/0046122 A1 | 2/2008 | Manzo et al. |
| 2008/0058776 A1 | 3/2008 | Jo et al. |
| 2008/0071208 A1 | 3/2008 | Voegele et al. |
| 2008/0103492 A1 | 5/2008 | Morley et al. |
| 2008/0177285 A1 | 7/2008 | Brock et al. |
| 2008/0243106 A1 | 10/2008 | Coe et al. |
| 2008/0287926 A1 | 11/2008 | El Kheir |
| 2008/0314181 A1 | 12/2008 | Schena |
| 2009/0030449 A1 | 1/2009 | Kawai et al. |
| 2009/0036902 A1 | 2/2009 | Dimaio et al. |
| 2009/0198253 A1 | 8/2009 | Omori |
| 2009/0216248 A1 | 8/2009 | Uenohara et al. |
| 2009/0216249 A1 | 8/2009 | Jinno et al. |
| 2009/0247821 A1 | 10/2009 | Rogers |
| 2009/0248039 A1 | 10/2009 | Cooper et al. |
| 2009/0275994 A1 | 11/2009 | Phan et al. |
| 2009/0299141 A1 | 12/2009 | Downey et al. |
| 2010/0004508 A1 | 1/2010 | Naito et al. |
| 2010/0023025 A1 | 1/2010 | Zeiner et al. |
| 2010/0082041 A1 | 4/2010 | Prisco |
| 2010/0094130 A1 | 4/2010 | Ninomiya et al. |
| 2010/0121347 A1 | 5/2010 | Jaspers |
| 2010/0160929 A1 | 6/2010 | Rogers et al. |
| 2010/0160940 A1 | 6/2010 | Lutze et al. |
| 2010/0170519 A1 | 7/2010 | Romo et al. |
| 2010/0225209 A1 | 9/2010 | Goldberg et al. |
| 2010/0286712 A1 | 11/2010 | Won et al. |
| 2010/0305595 A1 | 12/2010 | Hermann |
| 2010/0318099 A1 | 12/2010 | Itkowitz et al. |
| 2010/0318101 A1 | 12/2010 | Choi |
| 2010/0324551 A1 | 12/2010 | Gerhardt |
| 2010/0331859 A1 | 12/2010 | Omori |
| 2011/0087236 A1 | 4/2011 | Stokes et al. |
| 2011/0087238 A1 | 4/2011 | Wang et al. |
| 2011/0213346 A1 | 9/2011 | Morley et al. |
| 2011/0230867 A1 | 9/2011 | Hirschfeld et al. |
| 2011/0275901 A1 | 11/2011 | Shelton, IV |
| 2011/0276084 A1 | 11/2011 | Shelton, IV |
| 2011/0290854 A1 | 12/2011 | Timm et al. |
| 2011/0301419 A1 | 12/2011 | Craft et al. |
| 2012/0010628 A1 | 1/2012 | Cooper et al. |
| 2012/0027762 A1 | 2/2012 | Schofield |
| 2012/0031114 A1 | 2/2012 | Mueller et al. |
| 2012/0049623 A1 | 3/2012 | Nakayama |
| 2012/0095298 A1 | 4/2012 | Stefanchik et al. |
| 2012/0116163 A1 | 5/2012 | Lutze et al. |
| 2012/0132018 A1 | 5/2012 | Tang et al. |
| 2012/0143173 A1 | 6/2012 | Steege et al. |
| 2012/0158014 A1 | 6/2012 | Stefanchik et al. |
| 2012/0191245 A1 | 7/2012 | Fudaba et al. |
| 2012/0209292 A1 | 8/2012 | Devengenzo et al. |
| 2012/0232339 A1 | 9/2012 | Csiky |
| 2012/0253326 A1 | 10/2012 | Kleyman |
| 2012/0277762 A1 | 11/2012 | Lathrop et al. |
| 2012/0283745 A1 | 11/2012 | Goldberg et al. |
| 2012/0289973 A1 | 11/2012 | Prisco et al. |
| 2012/0289974 A1 | 11/2012 | Rogers et al. |
| 2012/0296341 A1 | 11/2012 | Seibold et al. |
| 2013/0123805 A1 | 5/2013 | Park et al. |
| 2013/0144274 A1 | 6/2013 | Stefanchik et al. |
| 2013/0172713 A1 | 7/2013 | Kirschenman |
| 2013/0172906 A1 | 7/2013 | Olson et al. |
| 2013/0245643 A1 | 9/2013 | Woodard et al. |

(56) References Cited

U.S. PATENT DOCUMENTS

| | | |
|---|---|---|
| 2013/0245647 A1 | 9/2013 | Martin et al. |
| 2013/0282027 A1 | 10/2013 | Woodard et al. |
| 2013/0304083 A1 | 11/2013 | Kaercher et al. |
| 2014/0005681 A1 | 1/2014 | Gee et al. |
| 2014/0018447 A1 | 1/2014 | McGovern et al. |
| 2014/0018780 A1 | 1/2014 | Hirscheld |
| 2014/0018960 A1 | 1/2014 | Itkowitz |
| 2014/0052152 A1 | 2/2014 | Au et al. |
| 2014/0076088 A1 | 3/2014 | Berkelman et al. |
| 2014/0114481 A1 | 4/2014 | Ogawa et al. |
| 2014/0142595 A1 | 5/2014 | Awtar et al. |
| 2014/0166023 A1 | 6/2014 | Kishi |
| 2014/0180308 A1 | 6/2014 | Von Grunberg |
| 2014/0188091 A1 | 7/2014 | Vidal et al. |
| 2014/0188159 A1 | 7/2014 | Steege |
| 2014/0200561 A1 | 7/2014 | Ingmanson et al. |
| 2014/0207150 A1 | 7/2014 | Rosa et al. |
| 2014/0229007 A1* | 8/2014 | Kishi .................. G06F 3/0346 700/257 |
| 2014/0230595 A1 | 8/2014 | Butt et al. |
| 2014/0249546 A1 | 9/2014 | Shvartsberg et al. |
| 2014/0263541 A1 | 9/2014 | Leimbach et al. |
| 2014/0263553 A1 | 9/2014 | Leimbach et al. |
| 2014/0276950 A1 | 9/2014 | Smaby et al. |
| 2014/0276951 A1 | 9/2014 | Hourtash et al. |
| 2014/0276956 A1 | 9/2014 | Crainich et al. |
| 2014/0277017 A1 | 9/2014 | Leimbach et al. |
| 2014/0350570 A1 | 11/2014 | Lee |
| 2015/0057499 A1 | 2/2015 | Erden et al. |
| 2015/0057702 A1 | 2/2015 | Edmondson et al. |
| 2015/0060517 A1 | 3/2015 | Williams |
| 2015/0066018 A1 | 3/2015 | Doll et al. |
| 2015/0105821 A1 | 4/2015 | Ward et al. |
| 2015/0142018 A1 | 5/2015 | Sniffin et al. |
| 2015/0150575 A1 | 6/2015 | Hartoumbekis et al. |
| 2015/0230869 A1 | 8/2015 | Shim et al. |
| 2015/0250547 A1 | 9/2015 | Fukushima et al. |
| 2015/0265355 A1 | 9/2015 | Prestel et al. |
| 2016/0022365 A1 | 1/2016 | Jensen et al. |
| 2016/0051274 A1 | 2/2016 | Howell et al. |
| 2016/0151115 A1 | 6/2016 | Karguth et al. |
| 2016/0220314 A1 | 8/2016 | Huelman et al. |
| 2016/0374766 A1 | 12/2016 | Schuh |
| 2017/0020615 A1 | 1/2017 | Koenig et al. |
| 2017/0245954 A1 | 8/2017 | Beira |
| 2017/0265951 A1 | 9/2017 | Grover et al. |
| 2017/0273749 A1 | 9/2017 | Grover et al. |
| 2017/0308667 A1 | 10/2017 | Beira et al. |
| 2017/0360522 A1 | 12/2017 | Beira |
| 2017/0367778 A1 | 12/2017 | Beira |
| 2018/0000472 A1 | 1/2018 | Beira |
| 2018/0000544 A1 | 1/2018 | Beira |
| 2018/0000550 A1 | 1/2018 | Beira |
| 2018/0008358 A1 | 1/2018 | Kostrzewski et al. |
| 2018/0028269 A1 | 2/2018 | Morel et al. |
| 2018/0055583 A1 | 3/2018 | Schuh et al. |
| 2018/0078439 A1 | 3/2018 | Cagle et al. |
| 2018/0110576 A1 | 4/2018 | Kopp et al. |
| 2018/0125519 A1 | 5/2018 | Beira et al. |
| 2018/0125592 A1 | 5/2018 | Beira |
| 2018/0242991 A1 | 8/2018 | Beira |
| 2018/0353252 A1 | 12/2018 | Chassot et al. |
| 2018/0360548 A1 | 12/2018 | Marshall et al. |

FOREIGN PATENT DOCUMENTS

| | | |
|---|---|---|
| CN | 101732093 A | 6/2010 |
| CN | 103717355 A | 4/2014 |
| DE | 43 03 311 A1 | 8/1994 |
| DE | 19652792 C2 | 5/1999 |
| DE | 10314827 B3 | 4/2004 |
| DE | 10314828 B3 | 7/2004 |
| DE | 10 2012 222 755 | 6/2014 |
| DE | 10 2014 205 036 A1 | 9/2015 |
| DE | 10 2014 205 159 A1 | 9/2015 |
| EP | 0 595 291 A1 | 5/1994 |
| EP | 0 621 009 A1 | 10/1994 |
| EP | 0 677 275 A2 | 10/1995 |
| EP | 1 254 642 A1 | 11/2002 |
| EP | 1 279 371 B1 | 12/2004 |
| EP | 1 886 630 A2 | 2/2008 |
| EP | 1 889 579 A2 | 2/2008 |
| EP | 2 058 090 A2 | 5/2009 |
| EP | 1 977 677 B1 | 8/2009 |
| EP | 2 095 778 A1 | 9/2009 |
| EP | 1 889 583 B1 | 4/2011 |
| EP | 2 377 477 B1 | 5/2012 |
| EP | 2 473 119 A2 | 7/2012 |
| EP | 2 305 144 B1 | 10/2012 |
| EP | 2 044 893 B1 | 7/2013 |
| EP | 2 653 110 A1 | 10/2013 |
| EP | 2 679 192 A2 | 1/2014 |
| EP | 2 736 680 A2 | 6/2014 |
| EP | 2 777 561 A1 | 9/2014 |
| EP | 2 837 340 A1 | 2/2015 |
| EP | 2 837 354 A1 | 2/2015 |
| EP | 2 554 131 B1 | 8/2015 |
| EP | 2 979 657 A1 | 2/2016 |
| EP | 2 783 643 B1 | 1/2019 |
| GB | 0 834 244 | 5/1960 |
| GB | 0 969 899 A | 9/1964 |
| JP | 2004-041580 A | 2/2004 |
| JP | 2007-290096 A | 11/2007 |
| JP | 2008-104620 A | 5/2008 |
| JP | 2009-018027 A | 1/2009 |
| KR | 20110032444 A | 3/2011 |
| KR | 20130031403 A | 3/2013 |
| WO | WO-82/00611 | 3/1982 |
| WO | WO-03/067341 A2 | 8/2003 |
| WO | WO-03/086219 A2 | 10/2003 |
| WO | WO-2004/052171 A2 | 6/2004 |
| WO | WO-2005/009482 A2 | 2/2005 |
| WO | WO-2005/046500 A1 | 5/2005 |
| WO | WO-2006/086663 A2 | 4/2006 |
| WO | WO-2007/133065 A1 | 11/2007 |
| WO | WO-2008/130235 A2 | 10/2008 |
| WO | WO-2009/091497 A2 | 7/2009 |
| WO | WO-2009/095893 A2 | 8/2009 |
| WO | WO-2009/145572 A2 | 12/2009 |
| WO | WO-2009/157719 A2 | 12/2009 |
| WO | WO-2010/019001 A2 | 2/2010 |
| WO | WO-2010/030114 A2 | 3/2010 |
| WO | WO-2010/050771 A2 | 5/2010 |
| WO | WO-2010/083480 A2 | 7/2010 |
| WO | WO-2010/096580 A1 | 8/2010 |
| WO | WO-2010/130817 A1 | 11/2010 |
| WO | WO-2011/025818 A1 | 3/2011 |
| WO | WO-2011/027183 A1 | 3/2011 |
| WO | WO-2011/123669 A1 | 10/2011 |
| WO | WO-2012/020386 A1 | 2/2012 |
| WO | WO-2012/049623 A1 | 4/2012 |
| WO | WO-2013/014621 A2 | 1/2013 |
| WO | WO-2014/012780 A1 | 1/2014 |
| WO | WO-2014/018447 A1 | 1/2014 |
| WO | WO-2014/067804 A1 | 5/2014 |
| WO | WO-2014/094716 A1 | 6/2014 |
| WO | WO-2014/094717 | 6/2014 |
| WO | WO-2014/094718 | 6/2014 |
| WO | WO-2014/094719 | 6/2014 |
| WO | WO-2014/145148 A2 | 9/2014 |
| WO | WO-2014/156221 A1 | 10/2014 |
| WO | WO-2014/201010 A1 | 12/2014 |
| WO | WO-2014/201538 A1 | 12/2014 |
| WO | WO-2015/081946 A1 | 6/2015 |
| WO | WO-2015/081947 A1 | 6/2015 |
| WO | WO-2015/088647 A1 | 6/2015 |
| WO | WO-2015/088655 A1 | 6/2015 |
| WO | WO-2015/111475 A1 | 7/2015 |
| WO | WO-2015/113933 A1 | 8/2015 |
| WO | WO-2015/129383 A1 | 8/2015 |
| WO | WO-2015/139674 A1 | 9/2015 |
| WO | WO-2015/175200 A1 | 11/2015 |
| WO | WO-2016/083189 A1 | 6/2016 |

(56) References Cited

FOREIGN PATENT DOCUMENTS

| WO | WO-2016/154173 | A1 | 9/2016 |
|---|---|---|---|
| WO | WO-2016/183054 | A1 | 11/2016 |
| WO | WO-01/6189284 | A1 | 12/2016 |
| WO | WO-2016/189284 | A1 | 12/2016 |
| WO | WO-2017/015599 | A1 | 1/2017 |
| WO | WO-2017/064301 | A1 | 4/2017 |
| WO | WO-2017/064303 | A1 | 4/2017 |
| WO | WO-2017/064305 | A1 | 4/2017 |
| WO | WO-2017/064306 | A1 | 4/2017 |
| WO | WO-2017/134077 | A1 | 8/2017 |
| WO | WO-2017/220978 | A1 | 12/2017 |
| WO | WO-2018/142112 | A1 | 8/2018 |
| WO | WO-2018/162921 | A1 | 9/2018 |

OTHER PUBLICATIONS

Partial International Search dated May 28, 2019 in Int'l PCT Patent Appl. Serial No. PCT/IB2019/050961.
International Search Report & Written Opinion dated Jul. 10, 2018 in Int'l PCT Patent Appl. Serial No. PCT/IB2018/053272.
Abbott, et al., "Design of an Endoluminal NOTES Robotic System," IEEE/RSJ International Conference on Intelligent Robots and Systems, San Diego, CA, pp. 410-416 (2007).
Aesculap Surgical Technologies, Aesculap® Caiman®, Advanced Bipolar Seal and Cut Technology Brochure, 6 pages (retrieved Aug. 31, 2015).
Arata, et al., "Development of a dexterous minimally-invasive surgical system with augmented force feedback capability," IEEE/RSJ International Conference on Intelligent Robots and Systems, pp. 3207-3212 (2005).
Çavuşoğlu, et al., "Laparoscopic Telesurgical Workstation," IEEE Transactions on Robotics and Automation,(15)4:728-739 (1999).
Dachs, et al., "Novel Surgical Robot Design: Minimizing the Operating Envelope Within the Sterile Field," 28th International Conference, IEEE Engineering in Medicine Biology Society, New York, pp. 1505-1508 (2006).
Dario, et al., "Novel Mechatronic Tool for Computer-Assisted Arthroscopy," IEEE Transactions on Information Technology in Biomedicine, 4(1):15-29 (Mar. 2000).
Focacci, et al., "Lightweight Hand-held Robot for Laparoscopic Surgery," IEEE International Conference on Robotics & Automation, Rome, Italy, pp. 599-604 (2007).
Guthart, et al., "The Intuitive™ Telesurgery System: Overview and Application," IEEE International Conference on Robotics & Automation, San Francisco, CA, pp. 618-621 (2000).
Ikuta, et al., "Development of Remote Microsurgery Robot and New Surgical Procedure for Deep and Narrow Space," IEEE International Conference on Robotics & Automation, Taipei, Taiwan, pp. 1103-1108 (2003).
Ikuta, et al., "Hyper Redundant Miniature Manipulator 'Hyper Finger' for Remote Minimally Invasive Surgery in Deep Area," IEEE International Conference on Robotics & Automation, Taipei, Taiwan, pp. 1098-1102 (2003).
International Search Report & Written Opinion dated Feb. 2, 2017 in Int'l PCT Patent Appl. Serial No. PCT/IB2016/001286.
International Search Report & Written Opinion dated Jan. 18, 2013 in Int'l PCT Patent Appl Serial No. PCT/IB2012/053786.
International Search Report dated Jan. 18, 2013 in Int'l PCT Patent Appl Serial No. PCT/IB2012/053786.
International Search Report dated Mar. 23, 2012 in Int'l PCT Patent Appl Serial No. PCT/IB2011/054476.
Ishii, et al., "Development of a New Bending Mechanism and Its Application to Robotic Forceps Manipulator," IEEE International Conference on Robotics & Automation, Rome, Italy, pp. 238-243 (2007).
International Search Report & Written Opinion dated May 23, 2016 in Int'l PCT Patent Appl Serial No. PCT/IB2015/002524.
International Search Report & Written Opinion dated Mar. 30, 2015 in Int'l PCT Patent Appl Serial No. PCT/EP2015/051473.
International Search Report & Written Opinion dated Apr. 26, 2016 in Int'l PCT Patent Appl Serial No. PCT/IB2015/002512.
International Search Report & Written Opinion dated May 24, 2016 in Int'l PCT Patent Appl Serial No. PCT/IB2015/002487.
International Search Report & Written Opinion dated Jun. 10, 2016 in Int'l PCT Patent Appl Serial No. PCT/IB2015/002533.
International Search Report & Written Opinion dated Jun. 13, 2016 in Int'l PCT Patent Appl Serial No. PCT/IB2015/002493.
International Search Report & Written Opinion dated Aug. 25, 2016 in Int'l PCT Patent Appl Serial No. PCT/IB2016/000542.
International Search Report & Written Opinion dated Sep. 2, 2016 in Int'l PCT Patent Appl Serial No. PCT/IB2016/000543.
Kobayashi, et al., "Small Occupancy Robotic Mechanisms for Endoscopic Surgery," International Conference on Medical Image Computing and Computer assisted Interventions, pp. 75-82 (2002).
Mayer, et al., "The Endo[PA]R System for Minimally Invasive Robotic Surgery," IEEE/RSJ International Conference on Intelligent Robots and Systems, Sendai, Japan, pp. 3637-3642 (2004).
Mitsuishi, et al., "Development of a Remote Minimally Invasive Surgical System with Operational Environment Transmission Capability," IEEE International Conference on Robotics & Automation, Taipei, Taiwan, pp. 2663-2670 (2003).
Nakamura, et al., "Multi-DOF Forceps Manipulator System for Laparoscopic Surgery-Mechanism miniaturized & Evaluation of New Interface," 4th International Conference on Medical Image Computing and Computer assisted Interventions (MICCAI2001), pp. 606-613 (2001).
Peirs, et al., "Design of an advanced tool guiding system for robotic surgery," IEEE International Conference on Robotics & Automation, Taipei, Taiwan, pp. 2651-2656 (2003).
Sallé, et al., "Optimal Design of High Dexterity Modular MIS Instrument for Coronary Artery Bypass Grafting," IEEE International Conference on Robotics & Automation, New Orleans, LA, pp. 1276-1281 (2004).
Seibold, et al., "Prototype of Instrument for Minimally Invasive Surgery with 6-Axis Force Sensing Capability," IEEE International Conference on Robotics & Automation, Barcelona, Spain, pp. 496-501 (2005).
Simaan et al., "Dexterous System for Laryngeal Surgery: Multi-Backbone Bending Snake-like Slaves for Teleoperated Dexterous Surgical Tool Manipulation," IEEE International Conference on Robotics & Automation, New Orleans, LA, pp. 351-357 (2004).
Stryker®, Endoscopy, Take a Look Around, Ideal Eyes™ FFD122 HD, Articulating Laparoscope Brochure, 2 pages (2009).
Swiss Search Report dated Jun. 4, 2012 in Swiss Patent Application No. CH 00702/12.
Tavakoli, et al., "Force Reflective Master-Slave System for Minimally Invasive Surgery," IEEE/RSJ International Conference on Intelligent Robots and Systems, Las Vegas, NV, pp. 3077-3082 (2003).
Taylor, et al., "Steady-Hand Robotic System for Microsurgical Augmentation," The International Journal of Robotics Research, 18(12):1201-1210 (1999).
www.cttc.co/technologies/maestro-non-robotic-dexterous-laproscopic-instrument-writs-providing-seven-degrees, "Maestro: Non-Robotic Dexterous Laproscopic Instrument With a Wrist Providing Seven Degrees of Freedom", accessed Nov. 12, 2015, 4 pages.
Yamashita, et al., "Development of Endoscopic Forceps Manipulator Using Multi-Slider Linkage Mechanisms," The 1st Asian Symposium on Computer Aided Surgery-Robotic and Image-Guided Surgery, Ibaraki, Japan, 4 pages (2005).
Zeus, "Robotic Surgical System" available at http://allaboutroboticsurgery.com/zeusrobot.html.
Extended European Search Report dated Mar. 18, 2020 in EP Patent Appl. Serial No. 19213231.4 (DM-1031 EP).
Partial International Search dated Apr. 1, 2020 in Int'l PCT Patent Appl. Serial No. PCT/IB2020/050039 (DM-1610).
U.S. Appl. No. 13/878,924, filed May 17, 2013.
U.S. Appl. No. 14/233,184 / U.S. Pat. No. 9,696,700, filed Jan. 16, 2014 / Jul. 4, 2017.
U.S. Appl. No. 15/116,509, filed Aug. 3, 2016.
U.S. Appl. No. 15/506,659, filed Feb. 24, 2017.
U.S. Appl. No. 15/536,562, filed Jun. 15, 2017.

(56) References Cited

OTHER PUBLICATIONS

U.S. Appl. No. 15/536,568, filed Jun. 15, 2017.
U.S. Appl. No. 15/536,573, filed Jun. 15, 2017.
U.S. Appl. No. 15/536,576, filed Jun. 15, 2017.
U.S. Appl. No. 15/633,611, filed Jun. 26, 2017.

* cited by examiner

DOCKING SYSTEM FOR MECHANICAL TELEMANIPULATOR

FIELD OF THE INVENTION

A docking system for a mechanical telemanipulator is provided. More particularly, a docking system is provided for a mechanical telemanipulator with a master-slave configuration wherein the movements of one or more master manipulators is reproduced in the movements of one or more slave manipulators. Even more particularly, it may be desirable for the operator of a mechanical telemanipulator with a master-slave configuration to dock or secure a master manipulator so as to temporarily prevent movement of a slave manipulator. Accordingly, the present invention is related to a docking system for a mechanical telemanipulator with a master-slave configuration that allows a user to safely secure the master manipulator or handle portion to prevent unwanted movements. Thus, the present invention is further related to a method of safely securing the handle or master manipulator of a mechanical telemanipulator with a master-slave configuration.

BACKGROUND OF THE INVENTION

The present docking system can be provided in connection with any mechanical telemanipulator, particularly those comprising a master-slave configuration. Optionally, the inventive docking system can be advantageously provided on a surgical platform comprising a mechanical telemanipulator with a master-slave configuration. In the surgical context, it is crucial that the operator of the mechanical telemanipulator (e.g., a telemanipulator designed to be used in minimally invasive surgery) be able to secure or dock the one or more handles or master manipulators of the mechanical telemanipulator so as to prevent movement of the slave manipulator. In the surgical context, the operator needs to have confidence that only desired movements of the slave manipulator will take place, particularly when portions of the slave manipulator are disposed within a patient's body. For example, the operator may need to dock the master manipulator to temporarily attend to other tasks in the operating room or to assess progress in the surgery before continuing.

Open surgery is still the standard technique for most surgical procedures. It has been used by the medical community for several decades and consists of performing the surgical tasks by a long incision in the abdomen or other body cavity, through which traditional surgical tools are inserted. However, due to the long incision, this approach is extremely invasive for the patient, resulting in substantial blood loss during the surgery and long and painful recovery periods in an in-patient setting.

In order to reduce the invasiveness of open surgery, laparoscopy, a minimally invasive technique, was developed. Instead of a single long incision, one or more smaller incisions are made in the patient through which appropriately sized surgical instruments and endoscopic cameras are inserted. Because of the low degree of invasiveness, laparoscopic techniques reduce blood loss and pain while also shortening hospital stays. When performed by experienced surgeons, these techniques can attain clinical outcomes similar to open surgery. However, despite the above-mentioned advantages, laparoscopy requires advanced surgical skills to manipulate the generally rigid and long instrumentation through small incisions in the patient.

Traditionally, laparoscopic instruments, such as graspers, dissectors, scissors and other tools, have been mounted on straight shafts. These shafts are inserted through small incisions into the patient's body and, because of that, their range of motion inside the body is reduced. The entry incision acts as a point of rotation, decreasing the surgeon's freedom for positioning and orientating the instruments inside the patient. Therefore, due to the drawbacks of currently available instrumentation, laparoscopic procedures are mainly limited to use in simple surgeries, while only a small minority of surgeons is able to use them in complex procedures.

In the context of laparoscopic surgery, and perhaps particularly in the context of laparoscopic surgeries where multiple surgical instruments may be attached and detached from a surgical platform with a master-slave configuration, it can be critical to be able to safely secure the master manipulator portion of the surgical platform such that instruments can safely be changed at the slave manipulator portion. In addition, laparoscopic procedures can be lengthy and complex, thus giving rise to circumstances where a surgeon may simply need to take a break or pause the surgery to attend to other tasks in the operating room. In such circumstances, it can be desirable to have a docking capability available so that the master manipulator can be safely secured, resulting in immobilization of the slave manipulator. This is particularly the case when surgical instruments are actually deployed in the surgical field (e.g., when a surgical instrument is positioned inside an incision in a patient) and a pause is necessary without re-positioning the surgical instrument.

The present applicants are unaware of any prior docking system that allows for safe and secure immobilization of a master manipulator in a mechanical telemanipulator with a master-slave configuration so as to prevent unwanted motion at the slave manipulator. Haptic devices with docking capabilities for the haptic arm are known, such as the Omni® line of devices by Sensable, but these do not include use of docking capabilities provided on a mechanical telemanipulator with a master-slave configuration. In particular, the present applicants are unaware of any similar docking system being provided in the context of surgical platforms including telemanipulators. While other surgical platforms are known, their movements are often controlled through electronic means whereby a computer dictates movement (or non-movement) of effectors. In certain such platforms, the system freezes by electronic control if the operator removes his hands from the controls or if his head moves away from an associated vision system. Such a configuration does not correspond to mechanical immobilization of a master manipulator so as to prevent movement of a slave manipulator in a mechanical telemanipulator comprising a master-slave configuration.

Accordingly, an aim of the present invention is to overcome a deficiency in the known art by providing a docking system for a mechanical telemanipulator. An additional aim is for the docking system to allow for secure immobilization of a master manipulator portion of the mechanical telemanipulator such that movement of a slave portion of the mechanical telemanipulator is prevented. An additional aim is to provide an operator of a mechanical telemanipulator with a method for securing the handle or master manipulator portion so as to prevent movement of the slave manipulator portion.

SUMMARY OF THE INVENTION

These aims and other advantages are realized in a new docking system for safely securing a master manipulator or handle of a mechanical telemanipulator. In one embodiment, the docking system can be used in the context of a master-slave-configured surgical platform wherein the operator wishes to secure the handle or master manipulator to prevent movement of the slave manipulator or surgical instrument. The docking system can be configured and deployed to allow for securing the system while changing surgical instruments or pausing use of the telemanipulator during a surgical procedure.

In various embodiments, the docking system is deployed in a method for securing a master manipulator or handle of a mechanical telemanipulator. In particular embodiments, the docking system may be deployed in a method for securing the handle or master manipulator of a surgical platform comprising a master-slave configuration to prevent movement of a slave manipulator or surgical instrument.

The docking system of the present invention can take on a number of physical configurations allowing for easy and secure docking of a master manipulator of a mechanical telemanipulator to a fixed element so as to temporarily prevent movement of a slave manipulator.

DETAILED DESCRIPTION OF THE INVENTION

Figure 1:
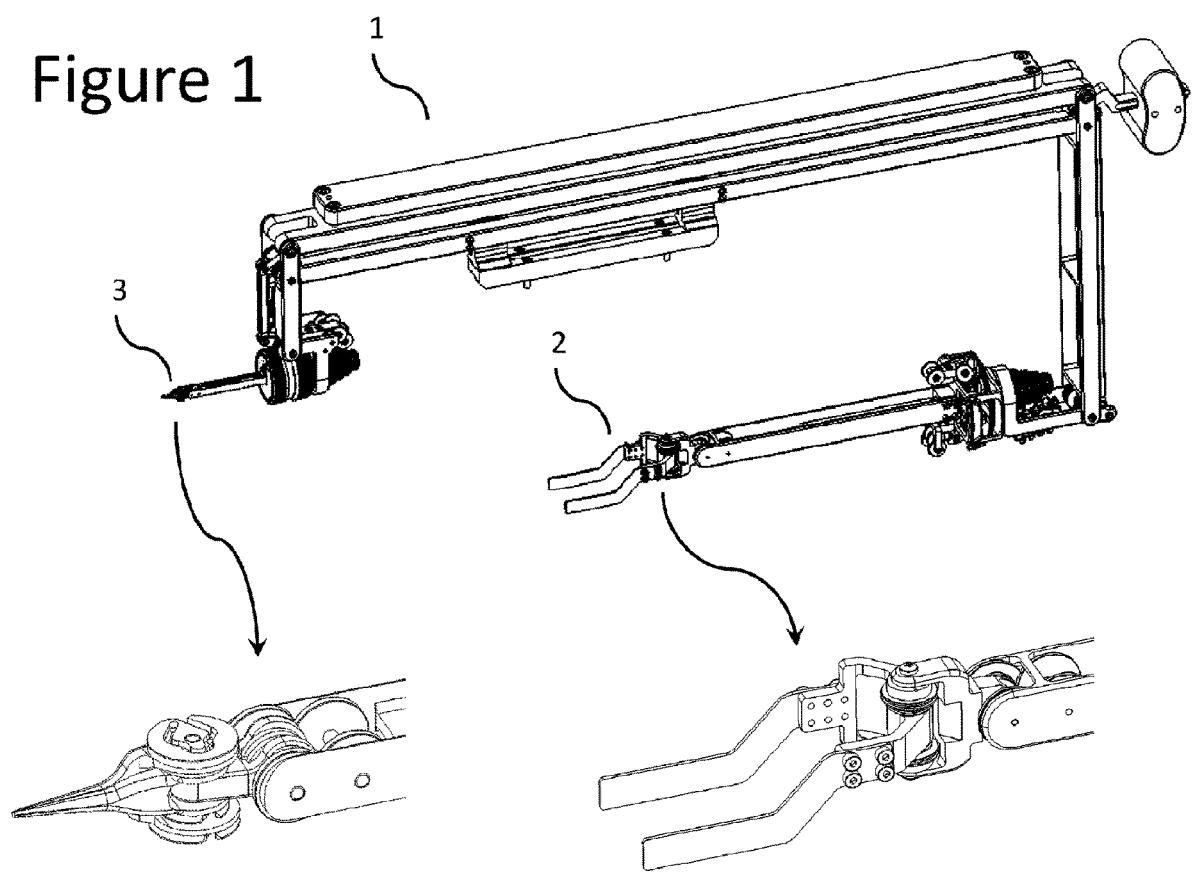
FIG. 1 shows a docking system disposed on a mechanical telemanipulator according to an embodiment of the present invention with close up views of a docking element disposed on a master manipulator and of a slave manipulator represented by a surgical instrument.

A docking system, according to an embodiment of the present invention, is intended to be used as an element of or in conjunction with a mechanical telemanipulator 1, like the one shown in FIG. 1. One of the key features of this kind of mechanical telemanipulator 1 lies in its master-slave architecture, which enables a natural replication of the user hand movements, on a proximal handle 2, by a distal instrument 3, on a remote location.

Figure 2:
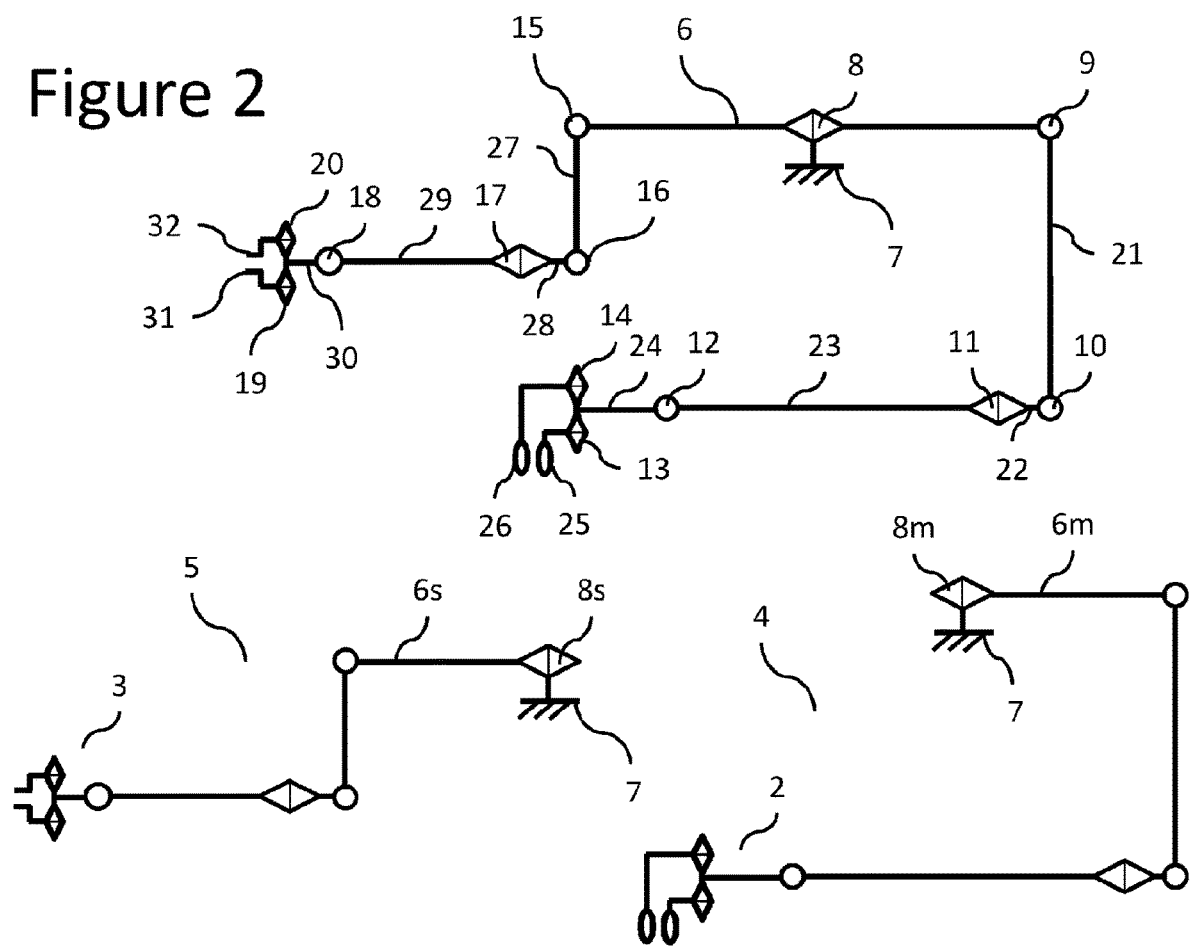
FIGS. 2 through 6 show the kinematics of a mechanical telemanipulator with various embodiments of a docking element according to the present invention.

According to FIG. 2, this mechanical telemanipulator 1 comprises: i) a master manipulator 4 having a corresponding number of master links 21, 22, 23, 24, 25, 26 interconnected by a plurality of master joints 9, 10, 11, 12, 13, 14, a ii) a handle 2 for operating the mechanical telemanipulator 1, connected to the distal end of the master manipulator 4, iii) a slave manipulator 5 having a number of slave links 27, 28, 29, 30, 31, 32 interconnected by a plurality of slave joints 15, 16, 17, 18, 19, 20; and iv) an end-effector 3 (instrument/tool or a gripper/holder) connected to the distal end of the slave manipulator 5. The configuration of the mechanical telemanipulator can also be described by considering the end-effector 3 to be part of the slave manipulator 5 and the handle 2 to be part of the master manipulator 4. In a broader sense, the links and joints composing the end-effector can be considered distal slave links and joints, while the links and joints composing the handle can be considered distal master links and joints.

More particularly, the kinematic chain formed by the plurality of articulated slave links 27, 28, 29, 30, 31, 32 and corresponding slave joints 15, 16, 17, 18, 19, 20 of the slave manipulator 5, is identical to the kinematic chain formed by the plurality of articulated master links 21, 22, 23, 24, 25, 26 and corresponding master joints 9, 10, 11, 12, 13, 14 of the master manipulator 4.

The end-effector 3 might optionally be adapted to be releasable from the proximal part of the slave manipulator 5. The master manipulator 4 and the slave manipulator 5 are connected to each other by a connecting link 6. This connecting link 6 is connected to a ground 7 by a first telemanipulator joint 8. This first telemanipulator joint 8 can be decomposed in a master joint $8m$ and slave joint $8s$, which can respectively be considered as the first proximal joints of the master manipulator 4 and the slave manipulator 5. In the same way, the connecting link 6 can be decomposed in a master link $6m$ and slave link $6s$, which can respectively be considered as the first proximal links of the master manipulator 4 and the slave manipulator 5.

With this kinematic model, the mechanical telemanipulator 1 has 7 independent degrees-of-freedom, (DOF), which enable the end-effector 3 to replicate handle 2 translations (3DOF), orientations (3DOF) and actuation (1DOF) in the vicinity of the remote manipulation area.

The mechanical telemanipulator device further comprises mechanical transmission systems arranged to kinematically connect the slave manipulator 5 with the master manipulator 4 such that the movement (angle or orientation of joint) applied on each master joint of the master manipulator 4 is reproduced by the corresponding slave joint of the slave manipulator 5. In order to improve the precision of the device, the replication of translational movements between handle 2 and end-effector 3 can be scaled down with a predetermined scaled ratio, which can advantageously be in the order of 2:1 or 3:1, if each master link is respectively, by way of example, two or three times longer than the corresponding slave link.

Figure 3:
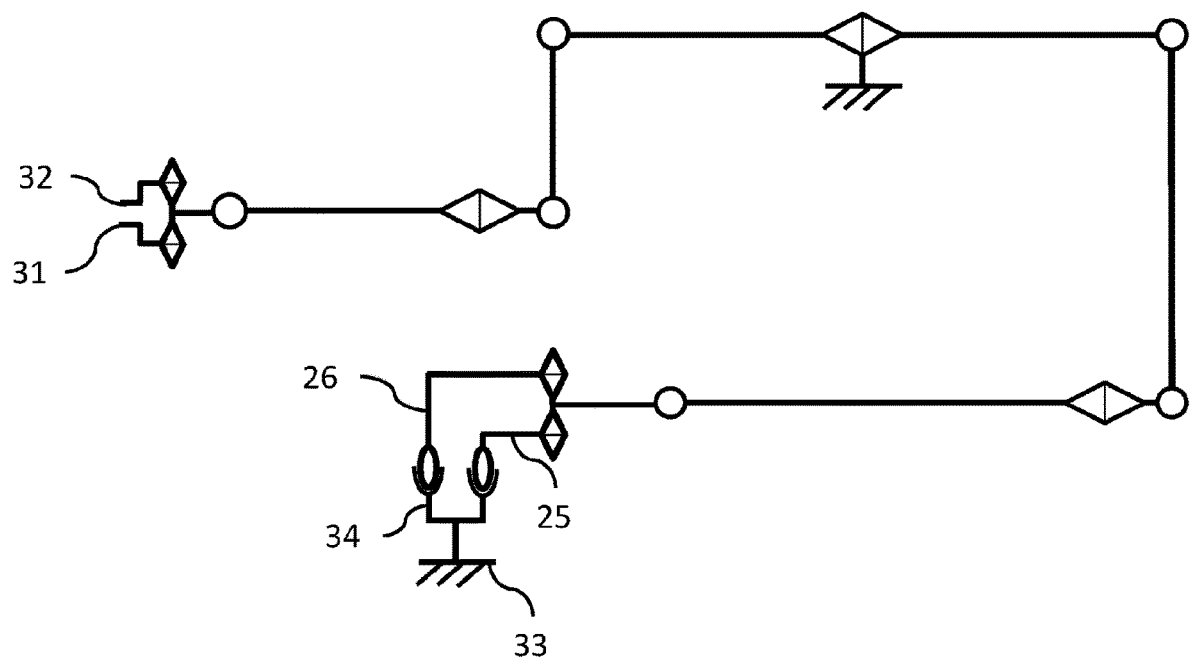

In order to allow the user to temporarily and safely release or dock the handle 2, in some embodiments of the current invention, the mechanical telemanipulator 1 can be provided with a docking system, being composed by at least one docking element 34 where at least one master link 25, 26 can be anchored (FIG. 3). In a general manner, the docking element can be attached to a reference body with a certain level of mobility and the docked point (where the master link is anchored to the docking point) might also be located not on the distal master links 25, 26 but on a more proximal link. As a result, all the master links from the proximal link to the link where the docked point is located, are able to move with the same mobility as the reference body. On the other hand, the links that are distal to the link where the docked point is located are not blocked. Due to the nature and design of the transmission system, the equivalent links of the slave manipulator 5 will also have the same mobility.

In the embodiment shown in FIG. 3, the reference element is a fixed ground 33. Therefore, this docking system enables the mechanical telemanipulator 1 to be completely blocked by attaching the handle links 25, 26 to a docking element 34. In this way, and given the fact that in this particular embodiment the telemanipulator 1 has non-redundant kinematics, the entire master manipulator 4 becomes blocked. As a consequence, due to the mechanical transmission system that connects the slave manipulator 5 to the master manipulator 4, all the links composing the mechanical telemanipulator 1 (from the master links 25, 26 to the slave links 31 and 32) become blocked, which completely avoids any unwanted movement of the end-effector in the vicinity of the remote manipulation area. In the context of a surgical platform, this would avoid any unwanted movement of end-effectors (surgical instruments) in the vicinity of the surgical field.

Figure 4:
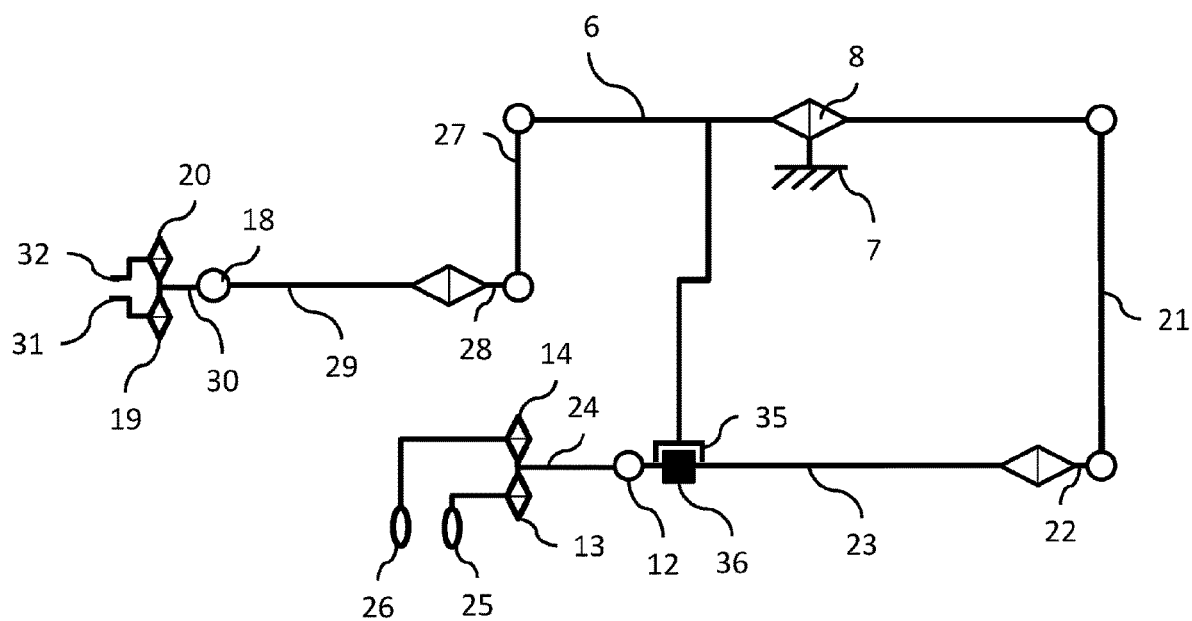

In other embodiments of the current invention, such as the one shown in FIG. 4, the reference element is the proximal master link 6, where the docking element 35 is attached and the docked point 36 is located on the non-distal master link 23. Therefore, all the master links from the proximal master link 6 to the master link 23 are able to move with the same mobility as the proximal master link 6, which consists of 1 DOF around the proximal joint 8. The same level of mobility is archived by the equivalent links of the slave manipulator 5. On the other hand, the master links 24, 25, 26 that are distal to the master link 23 attachment to the docked point 36 remain free to move. Due to the transmission system, the equivalent links 30, 31, 32 of the slave manipulator 5 will also be unblocked.

Figure 5:
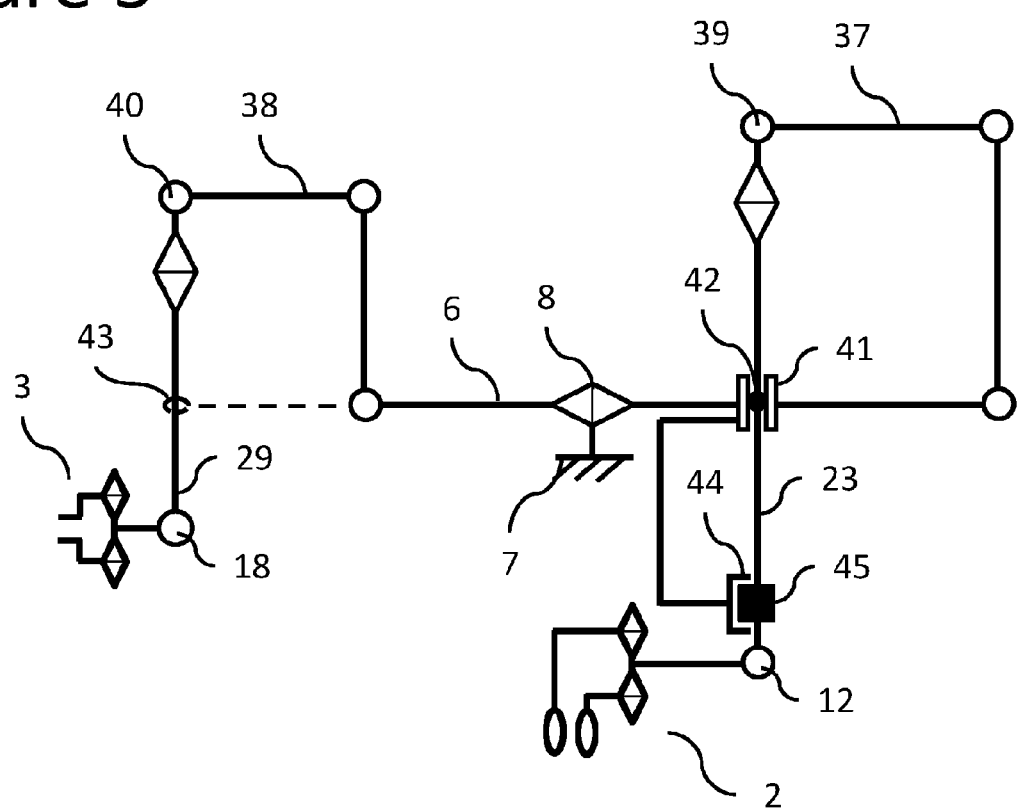

In another embodiment of this invention, shown in FIG. 5, the mechanical telemanipulator 1 comprises an additional DOF, compared to the mechanical telemanipulator 1 of the embodiment shown in FIGS. 1 to 4, with new master and slave links 37, 38 and new master and slave joints 39, 40, thus providing a total of 8 DOF. It further comprises a mechanical constraint system 41 which is configured to ensure that one master link 23 of the master manipulator 4 is guided or constrained to translate along and rotate about a fixed point 42, so that the corresponding slave link 29 of the slave manipulator 5 always translates along and rotates about a virtual point 43 in the vicinity of the remote manipulation area. This virtual point is also known as a remote-centre-of-motion, RCM. In this embodiment, the reference element is the mechanical constraint system 41, where the docking element 44 is attached. The docked point 45 is located on the non-distal master link 23. Therefore, all the master links from link 6 to link 23 are able to move with the same mobility as the mechanical constraint system 41, which consists of 2 DOF around the fixed point 42. The same level of mobility is achieved by the equivalent links of the slave manipulator 5, which have 2DOF around the RCM 43. On the other hand, the handle links 24, 25, 26 remain free to move. Due to the transmission system, the equivalent links 30, 31, 32 of the end-effector 3 will also be free.

Figure 6:
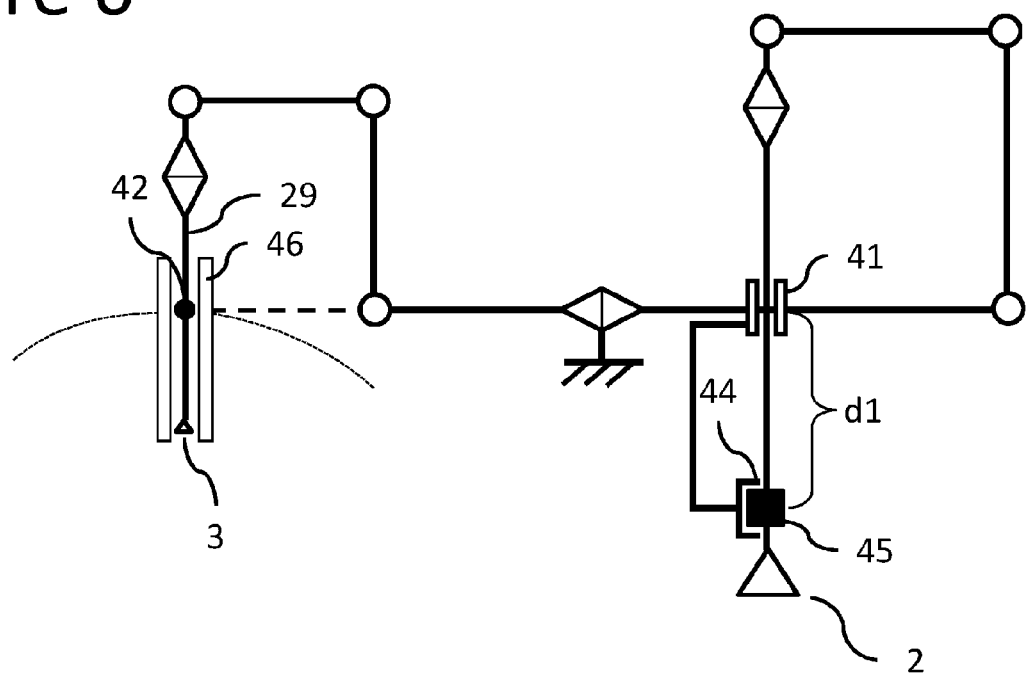

FIG. 6 shows the embodiment of FIG. 5 being used during a minimally invasive surgical procedure, where the end-effector 3 is inserted inside the patient's body through a trocar 46. The RCM is brought to the incision point. When the telemanipulator 1 is docked, the distance dl between the docked point 45 and the fixed point 42 can be set so that the end-effector 3 remains inside the trocar, and therefore in a safe position configuration to not allow for any involuntary movements of the end effector in the surgical field.

Figure 7:
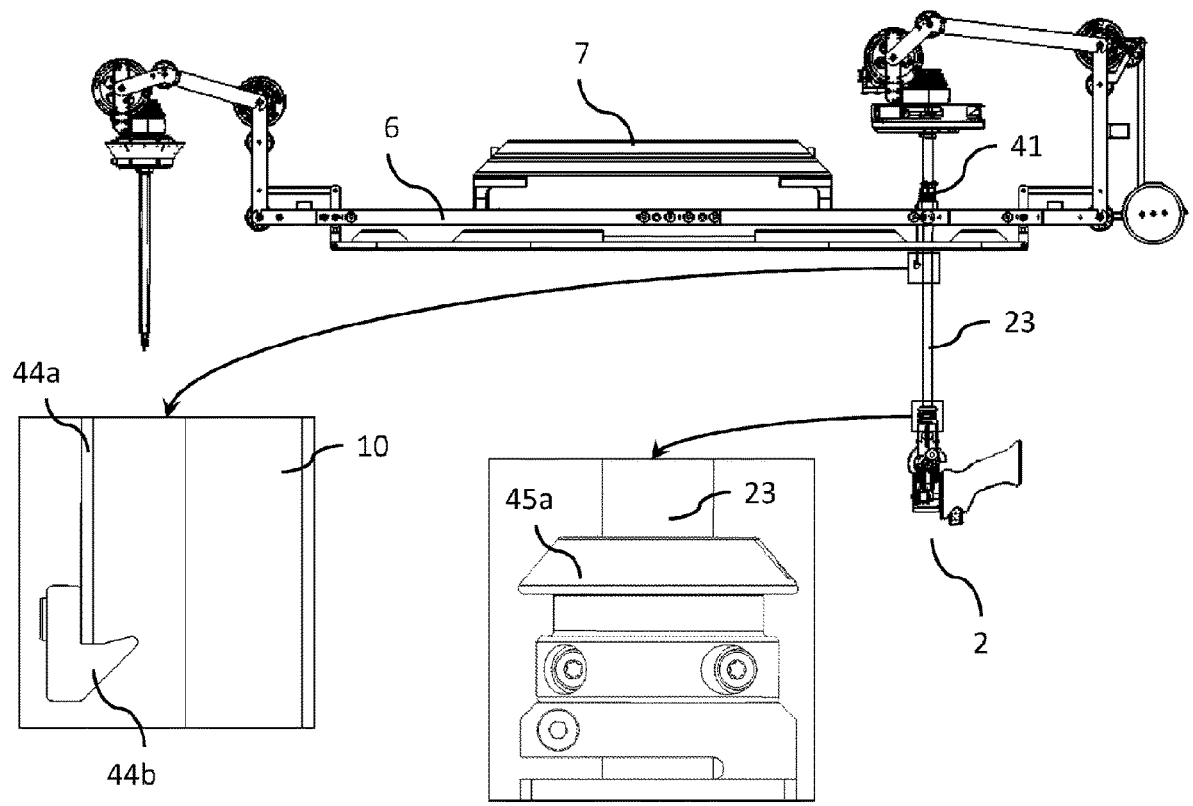
FIG. 7 shows close up views of various aspects of a docking element disposed on a mechanical telemanipulator according to an embodiment of the present invention.
Figure 8:
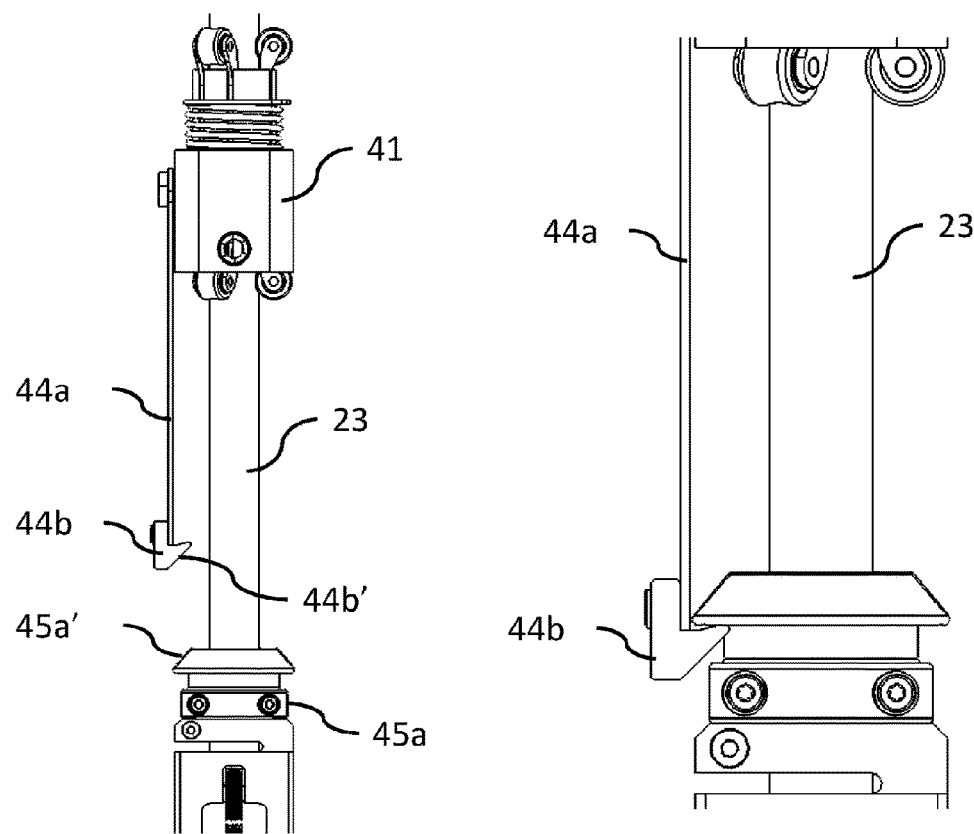
FIG. 8 shows perspective views of various aspects of a docking element according to an embodiment of the present invention.

FIG. 7 shows a possible design implementation of the embodiment of FIGS. 5 and 6. The docket point 45 comprises an axisymmetric component 45a, which is attached to the master link 23, while the docking system is mainly composed of a flexible blade 44a, attached to the constraint system 41, and a docking hook 44b.

Figure 9:
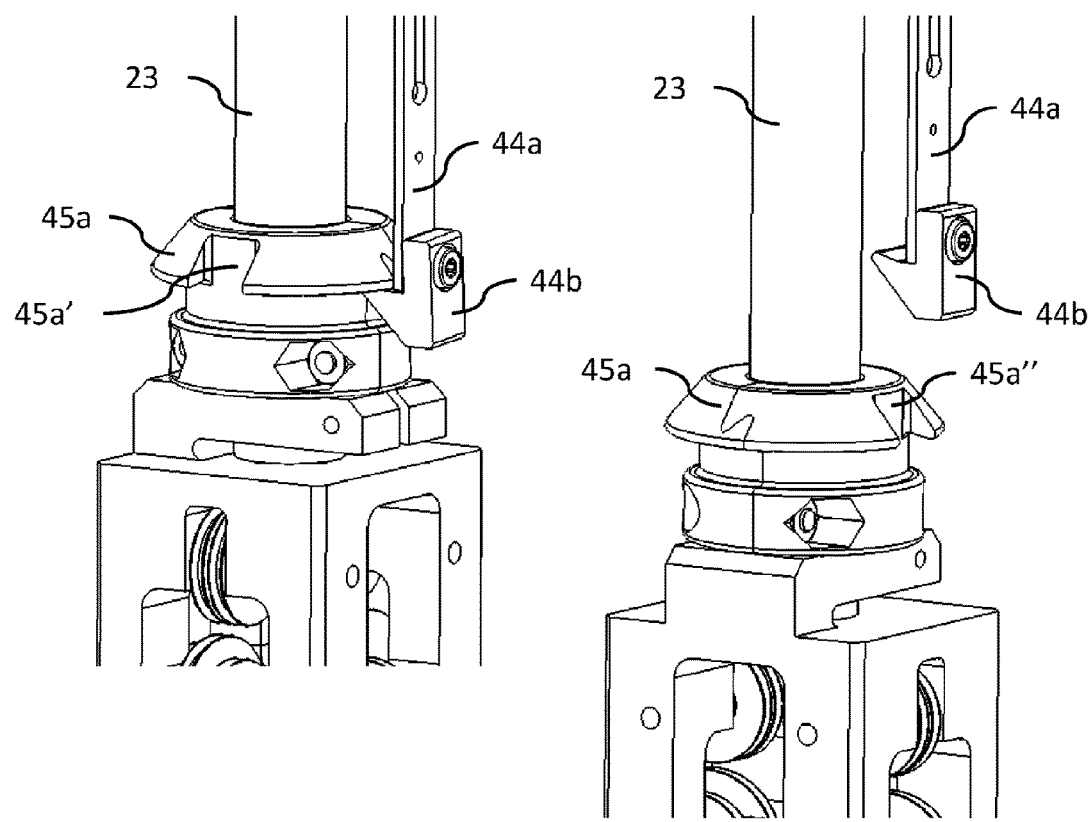
FIG. 9 shows perspective views of further aspects of a docking element according to an embodiment of the present invention.

In order to dock the mechanical telemanipulator 1, the master link 23 needs to slide upwards through the constraint system 41, causing at a certain point contact between the wedge surfaces 45a' and 44b' of the axisymmetric component 45a and the docking hook 44b. Then, the flexible blade 44a is deflected outwards until the wedge surfaces 45a' and 44b' are not in contact any more. In this position the mechanical telemanipulator is considered to be docked (upwards by gravity and downwards by the geometry of the axisymmetric component 45a and the docking hook 44b). In order to be undocked, the system master link 23 has to be twisted so that the docking hook 44b and the groove 45a" are aligned, as shown in FIG. 9.

Figure 10:
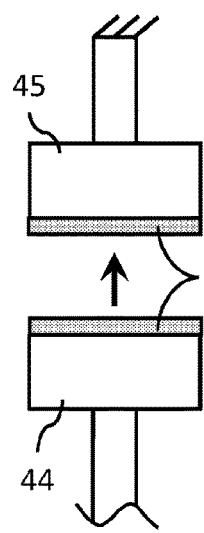
FIGS. 10 through 14 show various possible configurations of a docking element according to various embodiments of the present invention.
Figure 11:
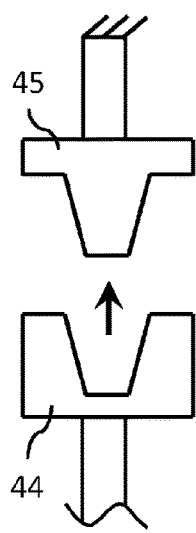
Figure 12:
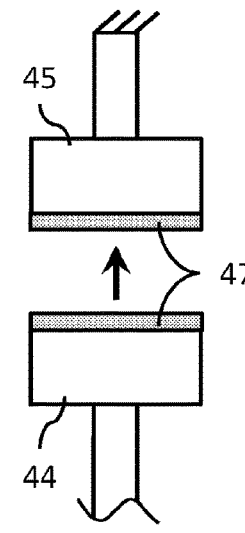
Figure 13:
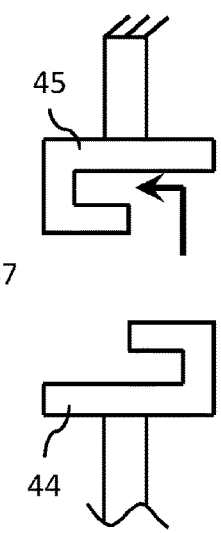
Figure 14:
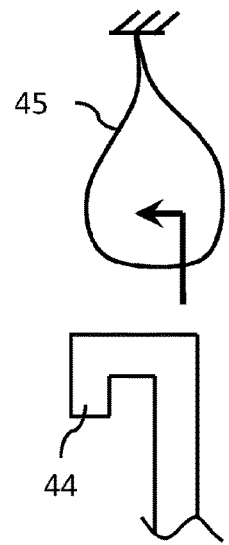

In other embodiments of the present invention, the docking system 44 and docked point 45 can take different shapes and solutions in other to guarantee the docking of the mechanical telemanipulator 1. In these embodiments, there are varied configurations in which the docking element is attached to the master link. For instance, FIG. 10 shows an embodiment wherein the attachment is made by a system with two magnets 46. FIG. 11 shows an embodiment were the attachment is made by friction forces. FIG. 12 shows an embodiment where the attachment is made by two Velcro surfaces 47. FIG. 13 shows an embodiment where the attachment is made by two matching geometries. FIG. 14 shows an embodiment were the docking system 44 takes the shape of a wire-like component where the docked point 45 can be hooked.

While this invention has been shown and described with reference to particular embodiments thereof, it will be understood by those skilled in the art that various changes in form and details may be made therein without departing from the spirit and scope of the invention as defined by the appended claims. Solely by way of example, one of skill in the art will understand that numerous shapes and solutions for the docking element and docked point of the inventive docking system are possible and that several exemplary embodiments have been presented herein.

The invention claimed is:
1. A docking system comprising:
 a surgical telemanipulator comprising a master manipulator and a slave manipulator, the master manipulator comprising at least one master link and a handle having at least one handle link, the slave manipulator comprising at least one slave link and an end-effector having at least one end-effector link; and
 at least one docking element disposed on at least one reference body of the master manipulator;
 wherein a master link of the at least one master link of the surgical telemanipulator comprises a docked element configured to be removeably attachable to the at least one docking element of the at least one reference body, and
 wherein, when the docked element is attached to the at least one docking element, the at least one master link has the same mobility as the at least one reference body while the at least one handle link and its corresponding end-effector link of the at least one end-effector link are configured to move independently of the at least one reference body and movement of the at least one master link causes movement at its corresponding slave link of the at least one slave link.
2. The docking system of claim 1, wherein attaching the docked element of the master link of the at least one master link to the at least one docking element results in reduced mobility of the surgical telemanipulator.

3. The docking system of claim 2, wherein the mobility of the master link of the at least one master link equals the mobility of the at least one reference body after the attachment of the master link of the at least one master link to the at least one docking element.

4. The docking system of claim 1 wherein the at least one end-effector is configured to replicate the at least one handle in three translations degrees-of-freedom, three orientations degrees-of-freedoms, and an actuation degree-of-freedom.

5. The docking system of claim 1, wherein the attachment between the docked element and the at least one docking element is accomplished by a system of magnets.

6. The docking system of claim 1, wherein the attachment between the docked element and the at least one docking element is accomplished by friction forces.

7. The docking system of claim 1, wherein the attachment between the docked element and the at least one docking element is accomplished by matching geometries, selected from the group consisting of rigid and compliant elements.

8. The docking system of claim 1, wherein the at least one docking element comprises a wire-like component where the docked element can be hooked.

9. The docking system of claim 1, wherein all the links of the surgical telemanipulator placed between the master link of the at least one master link attached to the at least one reference body and the at least one slave link have the same mobility as the at least one reference body.

10. The docking system of claim 1, wherein the surgical telemanipulator is part of a surgical platform to perform open and minimally invasive surgical procedures comprising a surgical instrument with proximal and distal extremities adapted to be placed in a minimally invasive trocar with a first length.

11. The docking system of claim 10, wherein a reduced mobility of the at least one slave link causes the distal extremity of the surgical instrument to be located within the first length of the minimally invasive trocar.

\* \* \* \* \*